United States Patent [19]

Mahieu et al.

[11] Patent Number: 5,788,992
[45] Date of Patent: Aug. 4, 1998

[54] ALKYL N-(HYDROXYALKYL) CARBAMATES AND THEIR APPLICATION IN COSMETICS, MORE PARTICULARLY IN HAIR COMPOSITIONS

[75] Inventors: Claude Mahieu, Paris; Eric Bollens, Saint Maurice; Daniele Cauwet-Martin, Paris, all of France

[73] Assignee: L'Oreal, Paris, France

[21] Appl. No.: 384,146

[22] Filed: Feb. 6, 1995

[30] Foreign Application Priority Data

Feb. 7, 1994 [FR] France ................. 94 01341

[51] Int. Cl.$^6$ .......................................... A61K 7/06
[52] U.S. Cl. .................. 424/70.1; 424/401; 424/450; 424/47; 514/844; 514/845; 514/846; 514/937; 514/944; 560/160
[58] Field of Search ................... 424/401, 70.1, 424/450, 47; 514/844, 845, 846, 937; 560/944, 160

[56] References Cited

U.S. PATENT DOCUMENTS

| | | | |
|---|---|---|---|
| 2,808,402 | 10/1957 | Boettner | 260/211 |
| 5,149,860 | 9/1992 | Zysman et al. | 560/160 |
| 5,198,470 | 3/1993 | Zysman et al. | 514/785 |
| 5,354,510 | 10/1994 | Vanlerberghe et al. | 252/548 |

FOREIGN PATENT DOCUMENTS

| | | |
|---|---|---|
| A-0420722 | 4/1991 | European Pat. Off. |
| A-0577506 | 1/1994 | European Pat. Off. |
| A-2315991 | 1/1977 | France |
| A-2416008 | 8/1979 | France |
| A-0450527 | 10/1991 | France |

OTHER PUBLICATIONS

Derwent Abstract of EP-A-0577506, (1994).
Derwent Abstract of FR-A-2315991, (1977).
Derwent Abstract of FR-A-2416008, (1979).

*Primary Examiner*—Jyothsan Venkat
*Attorney, Agent, or Firm*—Finnegan, Henderson, Farabow, Garrett & Dunner, L.L.P.

[57] ABSTRACT

New compounds of formula (I):

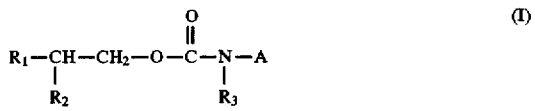

in which: $R_1$ represents a $C_4$–$C_{18}$ alkyl or alkylene radical, $R_2$ represents a $C_2$–$C_{16}$ alkyl or alkylene radical, $R_3$ represents a hydrogen atom or a $C_1$–$C_6$ alkyl radical, and A represents a non-ionic hydrophilic group, as well as a cosmetic composition containing these compounds and the use of such a cosmetic composition in hair treatment.

11 Claims, No Drawings

ALKYL N-(HYDROXYALKYL) CARBAMATES AND THEIR APPLICATION IN COSMETICS, MORE PARTICULARLY IN HAIR COMPOSITIONS

The present invention is directed to new alkyl N-(hydroxyalkyl)carbamates and their process of preparation. The present invention is also directed to cosmetic compositions containing these compounds. More particularly, the present invention is directed to the use of such compositions in hair treatment.

The subject of the present invention is therefore compounds of the formula (I):

$$R_1-\underset{\underset{R_2}{|}}{CH}-CH_2-O-\overset{\overset{O}{\|}}{C}-\underset{\underset{R_3}{|}}{N}-A \quad (I)$$

in which:
- $R_1$ represents an alkyl or alkylene radical having from 4 to 18 carbon atoms;
- $R_2$ represents an alkyl or alkylene radical having from 2 to 16 carbon atoms;
- $R_3$ represents a hydrogen atom or an alkyl radical having from 1 to 6 carbon atoms; and
- A represents a non-ionic hydrophilic group.

Preferably, $R_1$ represents an alkyl radical having from 4 to 14 carbon atoms; $R_2$ represents an alkyl radical having from 2 to 12 carbon atoms; and $R_3$ represents a hydrogen atom or a methyl radical.

Preferably, A represents a radical of the formula:

$$-(CH_2)_n-(CHOH)_m-Z$$

in which: n represents an integer equal to 0 or 1; m represents an integer ranging from 0 to 5; and Z is a monohydroxylated or polyhydroxylated alkyl radical having from 1 to 4 carbon atoms.

Preferably, Z is chosen from the group comprising the radicals:

$$-CH_2OH \quad -CH_2-CH_2OH \quad -CH(CH_2OH)_2$$

$$-C(CH_2OH)_3 \quad -\underset{\underset{CH_3}{|}}{C}(CH_2OH)_2 \quad -\underset{\underset{CH_3}{|}}{CH}-CH_2OH \quad \text{and}$$

$$-\underset{\underset{CH_3}{|}}{\overset{\overset{CH_3}{|}}{C}}-CH_2OH.$$

More preferably, Z is chosen from the group comprising the radicals:
—$CH_2OH$ and —$C(CH_2OH)_3$.

Mention may particularly be made, among the preferred compounds corresponding to formula (I), of:
- N-2-ethylhexyloxycarbonyl-N-methyl-D-glucamine;
- N-2-hexyldecyloxycarbonyl-N-methyl-D-glucamine;
- N-2-butyloctyloxycarbonyl-N-methyl-D-glucamine;
- N-2-decyltetradecyloxycarbonyl-N-methyl-D-glucamine;
- N-2-dodecylhexadecyloxycarbonyl-N-methyl-D-glucamine;
- N-2-decyltetradecyloxycarbonyl-D-glucamine;
- N-2-hexyldecyloxycarbonyl-D-glucamine;
- 3-[N-(2-decyltetradecyloxycarbonyl)amino]-1,2-propanediol;
- 2-[N-(2-decyltetradecyloxycarbonyl)amino]-2-hydroxymethyl-1,3-propanediol;
- 2-[N-(2-hexyldecyloxycarbonyl)amino]-1-ethanol; and
- 2-[N-(2-decyltetradecyloxycarbonyl)amino]-1-ethanol.

The present invention is also directed to a process for the preparation of compounds of formula (I). This process comprises reacting, in a solvent, an aminoalcohol of formula $R_3$—NH—A with a compound of formula (II):

$$R_1-\underset{\underset{R_2}{|}}{CH}-CH_2-O-\overset{\overset{O}{\|}}{C}-X \quad (II)$$

$R_1$, $R_2$, $R_3$ and A having the same definitions as those provided above, and X representing a halogen atom, preferably a chlorine atom, or a radical derived from an azole, preferably a radical arising from an imidazole such as that of formula (III):

$$-N\underset{\diagdown}{\diagup}\overset{\diagdown}{\underset{\diagup}{}}N \quad (III)$$

Any compatible solvent can be used in accordance with the present invention. Preferably the solvent is an inert solvent, meaning the solvent does not react with the aminoalcohol or with the compound of formula (II). It is possible to use, as an inert solvent, dichloromethane, 1,2-dichloroethane, 1,1,1-trichloroethane, chloroform, acetonitrile, toluene, dioxane, tetrahydrofuran, 1,2-dimethoxyethane, cyclohexane, water or a mixture of these solvents.

The reaction is preferably carried out at a temperature which ranges from $-5°$ C. to $50°$ C. and more preferably is less than $10°$ C.

The reaction can be carried out in the presence of a base. The base can be chosen from alkali metal or alkaline-earth metal hydroxides, sodium hydrogencarbonate, alkali metal alkoxides, alkali metal hydrides or tertiary amines such as pyridine or triethylamine. Sodium hydrogencarbonate is preferably used.

Another subject of the present invention is a cosmetic composition comprising, in a cosmetically acceptable vehicle, at least one compound of formula (I) as defined above. More preferably, but not exclusively, the cosmetic composition is a hair composition.

It is well-known that hair is sensitized or weakened to various degrees by the effect of atmospheric agents as well as by the repeated effect of various hair treatments such as permanent waves, hair straightening, dyeing or bleaching. The hair resultantly becomes rough to the touch and loses its shiny appearance. The hair is also difficult to disentangle and to style. It is therefore necessary, in the field of hair treatment, to use treatment agents in hair products with the aim of repairing the damage to which the hair has been subjected. These treatment agents have to contribute excellent properties to the hair such as disentangling, sheen, liveliness and a pleasant feel.

It has now been unexpectedly and surprisingly discovered that the compounds of formula (I), as defined above, have excellent properties, such as, when used in hair compositions, they confer styling, smoothing and coating effects to the hair and facilitate its disentangling. The compounds of formula (I), as defined above, are therefore very advantageous in hair treatment.

In the compositions according to the invention, the compounds of formula (I) are preferably present at a concentration which ranges from 0.001 to 15% by weight, and more preferably from 0.1 to 10% by weight, with respect to the total weight of the composition.

The compositions can be provided in the form of a monophase or polyphase aqueous or aqueous/alcoholic lotion, a monophase or polyphase gel, an emulsion, a cream, a vesicular dispersion, a foam, or a spray.

The hair compositions can be provided in the form of a shampoo, a conditioner which is or is not to be rinsed, compositions for permanent waving, hair straightening, dyeing or bleaching, compositions to be rinsed, compositions to be applied before or after a dyeing, a permanent waving or a hair straightening or alternatively compositions to be applied between the two stages of a permanent waving or a hair straightening.

The compositions can moreover contain conventional cosmetic additives chosen from fatty substances, organic solvents, silicones, thickeners, emollients, surface-active agents, anionic, cationic, non-ionic or amphoteric polymers, anti-foaming agents, hair conditioning agents such as proteins or vitamins, treating agents (anti-hair-loss or anti-dandruff agents), dyes, fragrances, preserving agents and propellants.

More preferably, as fatty substance, use can be made of an oil, a wax or a mixture thereof, fatty acids, fatty alcohols, fatty acid esters such as $C_6$ to $C_{18}$ fatty acid triglycerides, petroleum jelly, paraffin, lanolin, and hydrogenated and acetylated lanolin.

Mention may be made, among oils, of mineral, animal or vegetable oils, synthetic oils, and especially liquid paraffin, castor oil, jojoba oil and sesame oil, as well as silicon oils and gums and isoparaffins.

Mention may be made, among waxes, of animal, vegetable, inorganic or synthetic waxes, and especially beeswax, candelilla wax, ozocerites, microcrystalline waxes and silicone waxes and resins.

Mention may more preferably be made, among the organic solvents ordinarily used in cosmetic compositions, of lower $C_1$ to $C_6$ monoalcohols or polyalcohols such as ethanol, isopropanol, ethylene glycol, diethylene glycol, propylene glycol and glycerol.

The thickening agents can preferably be chosen from sodium alginate, gum arabic, cellulose derivatives such as methyl cellulose, hydroxymethyl cellulose, hydroxyethyl cellulose, hydroxypropyl cellulose and hydroxypropylmethyl cellulose, guar gum or its derivatives, xanthan gum, scleroglucans and crosslinked polyacrylic acids.

It is possible to use, as surface-active agents and as polymers, all those which are well-known in the state of the art, particularly for their use in hair compositions.

The compositions can be provided in the form of a vesicular dispersion of ionic or non-ionic amphiphilic lipids. These may preferably be prepared by swelling the lipids in an aqueous solution in order to form spherules dispersed in the aqueous medium as described in Standish & Watkins, J. Mol. Biol., 13, 238 (1965) and in French Patent Nos. FR-A-2,315,991 and FR-A-2,416,008, the disclosures of all of which are incorporated herein by reference. The various types of preparation processes are described in "Les liposomes en biologie cellulaire et pharmacologie" [Liposomes in cell biology and pharmacology], published by INSERM/ John Libery Eurotext, 1987, pages 6 to 18, the disclosure of which is also incorporated herein by reference.

The pH of the compositions according to the invention generally ranges from 4 to 8 and preferably ranges from 5 to 7.

Another subject of the invention is the use of a composition as defined above in hair treatment and a process for hair treatment which comprises applying a composition as defined above to the hair.

A number of examples demonstrating the preparation of compounds according to the invention and cosmetic compositions containing them will now be given by way of illustration and without any limiting nature.

EXAMPLE 1

Preparation of N-2-ethylhexyloxy-carbonyl-N-methyl-D-glucamine 117 g (0.6 mol) of N-methyl-D-glucamine were dissolved in a reactor in a mixture of 800 ml of water and 400 ml of tetrahydrofuran and then 201.6 g (2.4 mol) of sodium hydrogencarbonate were dispersed.

115.6 g (0.6 mol) of 2-ethylhexyl chloroformate were added dropwise, while maintaining the temperature of the reaction mixture at 5° C., and then the reaction mixture was allowed to react for 3 hours with stirring at 5° C. and overnight at rest at room temperature.

The reaction mixture was then filtered and concentrated; the pasty residue obtained was dissolved in 2 liters of acetone and then filtered after cooling to 5° C. The crystalline product collected was dried.

105 g (yield 50%) of N-2-ethylhexyloxycarbonyl-N-methyl-D-glucamine were obtained.

Melting point: 74.2° C.

| | ELEMENTAL ANALYSIS: | | | |
|---|---|---|---|---|
| | % C | % H | % O | % N |
| Calculated | 54.68 | 9.46 | 31.87 | 3.99 |
| Found | 54.73 | 9.48 | 31.95 | 3.92 |

EXAMPLE 2

Preparation of N-2-hexyldecyloxycarbonyl-N-methyl-D-glucamine

The compound was prepared according to the same procedure as Example 1, by using:

70.2 g (0.36 mol) of N-methyl-D-glucamine dissolved in a mixture of 60 ml of water and 80 ml of tetrahydrofuran;

20.96 g (1.44 mol) of sodium hydrogen-carbonate; and 109.62 g (0.36 mol) of 2-hexyldecyl chloroformate.

The solid residue resulting from the reaction mixture was recrystallized from one liter of acetone and then recrystallized a second time from 0.5 liter of acetone. After cooling at 0° C. for 12 hours, the crystalline product was recovered and dried.

100 g (yield 60%) of N-2-hexyldecyloxycarbonyl-N-methyl-D-glucamine were obtained.

Melting point: 70.6° C.

| | ELEMENTAL ANALYSIS: | | | |
|---|---|---|---|---|
| | % C | % H | % O | % N |
| Calculated | 62.17 | 10.65 | 24.16 | 3.02 |
| Found | 62.27 | 10.56 | 24.26 | 3.10 |

EXAMPLE 3

Preparation of N-2-butyloctyloxycarbonyl-N-methyl-D-glucamine

The compound was prepared according to the same procedure as Example 1, by using:

78 g (0.4 mol) of N-methyl-D-glucamine;

134.4 g (1.6 mol) of sodium bicarbonate; and 99.4 g (0.4 mol) of 2-butyloctyl chloroformate.

62 g of N-2-butyloctyloxycarbonyl-N-methyl-D-glucamine were obtained in the form of a white powder whose melting point was 77° C.

| ELEMENTAL ANALYSIS: | | | | |
|---|---|---|---|---|
| | % C | % H | % O | % N |
| Calculated | 58.94 | 10.24 | 3.44 | 27.48 |
| Found | 59.57 | 10.30 | 3.44 | 27.34 |

EXAMPLE 4

Preparation of N-2-decyltetradecyloxycarbonyl-N-methyl-D-glucamine

The compound was prepared according to the same procedure as Example 1, by using:

39 g (0.2 mol) of N-methyl-D-glucamine;

67.2 g (0.8 mol) of sodium bicarbonate; and 83.3 g (0.2 mol) of 2-decyltetradecyl chloroformate.

58 g of N-2-decyltetradecyloxycarbonyl-N-methyl-D-glucamine were obtained in the form of a white powder whose melting point was 63° C.

| ELEMENTAL ANALYSIS: | | | | |
|---|---|---|---|---|
| | % C | % H | % O | % N |
| Calculated | 66.74 | 11.38 | 2.43 | 19.45 |
| Found | 66.49 | 11.41 | 2.65 | 19.67 |

EXAMPLE 5

Preparation of N-2-dodecylhexadecyloxycarbonyl-N-methyl-D-glucamine

The compound was prepared according to the same procedure as Example 1, by using:

78 g (0.4 mol) of N-methyl-D-glucamine;

134.4 g (1.6 mol) of sodium bicarbonate; and 189 g (0.4 mol) of 2-dodecylhexadecyl chloroformate.

163 g of N-2-dodecylhexadecyloxycarbonyl-N-methyl-D-glucamine were obtained in the form of a white powder whose melting point was 54° C.

| ELEMENTAL ANALYSIS: | | | | |
|---|---|---|---|---|
| | % C | % H | % O | % N |
| Calculated | 68.55 | 11.74 | 2.38 | 17.54 |
| Found | 68.42 | 11.64 | 2.22 | 17.72 |

EXAMPLE 6

Preparation of N-2-decyltetradecyloxycarbonyl-D-glucamine 36.2 g (0.2 mol) of D-glucamine were dissolved in 100 ml of water in a 1000 ml reactor. 135 ml of tetrahydrofuran and then 67.2 g (0.8 mol) of sodium bicarbonate were added. The mixture was brought to −2° C. with stirring and then 83.3 g (0.2 mol) of 2-decyltetradecyl chloroformate were added dropwise over 150 minutes. At the end of the addition, the mixture was left for 2 hours at 0° C. and was then left to progressively return, also over 2 hours, to 25° C. The insoluble material was removed on sintered glass and concentration to dryness was then carried out with a rotary evaporator.

The residue was recrystallized from one liter of acetone and this operation was repeated once from one liter of acetone and once from one liter of ethyl acetate/acetone mixture (1/1 vol/vol).

61 g of N-2-decyltetradecyloxycarbonyl-D-glucamine were obtained in the form of a white powder whose melting point was 82° C.

| ELEMENTAL ANALYSIS: | | | | |
|---|---|---|---|---|
| | % C | % H | % O | % N |
| Calculated | 66.27 | 11.30 | 2.49 | 19.93 |
| Found | 66.41 | 11.34 | 2.44 | 20.01 |

EXAMPLE 7

Preparation of N-2-hexyldecyloxycarbonyl-D-glucamine

The compound was prepared according to the same procedure as Example 6, by using:

46.8 g (0.24 mol) of D-glucamine;

80.6 g (0.96 mol) of sodium bicarbonate; and 73.08 g (0.24 mol) of 2-hexyldecyl chloroformate.

70 g of N-2-hexyldecyloxycarbonyl-D-glucamine were obtained in the form of white powder whose melting point was 81° C.

EXAMPLE 8

Preparation of 3-[N-(2-decyltetradecyloxycarbonyl)amino]-1,2-propanediol

The compound was prepared according to the same procedure as Example 6, by using:

18.2 g (0.2 mol) of 3-amino-1,2-propanediol;

67.2 g (0.8 mol) of sodium bicarbonate; and 83.3 g (0.2 mol) of 2-decyltetradecyl chloroformate.

95 g of an amber oil were obtained, which oil was purified on silica using dichloromethane/methanol mixtures (from 10/0 to 9/1 vol/vol).

80 g of a white wax were obtained, the purity of which was monitored by thin layer chromatography (dichloromethane/methanol eluent: 95/5 vol/vol, $R_f=0.34$).

| ELEMENTAL ANALYSIS: | | | | |
|---|---|---|---|---|
| | % C | % H | % O | % N |
| Calculated | 71.29 | 12.18 | 2.97 | 13.57 |
| Found | 70.88 | 12.29 | 2.87 | 14.07 |

EXAMPLE 9

Preparation of 2-[N-(2-decyltetradecyloxycarbonyl)amino]-2-hydroxymethyl-1,3-propanediol The compound was prepared according to the same procedure as Example 6, by using:

24.2 g (0.2 mol) of tris(hydroxymethyl) aminomethane;
67.2 g (0.8 mol) of sodium bicarbonate; and
83.3 g (0.2 mol) of 2-decyltetradecyl chloroformate.

After reaction and purification on silica (heptane/ethyl acetate eluent: 7/3 then 6/4 vol/vol), 40 g of a white wax were obtained, the melting point of which was 51° C. and the purity of which was verified by thin layer chromatography (dichloromethane/methanol: 29/1 vol/vol; $R_f=0.45$)

| ELEMENTAL ANALYSIS: | | | | |
|---|---|---|---|---|
| | % C | % H | % O | % N |
| Calculated | 69.46 | 11.78 | 2.78 | 15.97 |
| Found | 69.42 | 11.81 | 2.75 | 15.87 |

EXAMPLE 10

Preparation of 2-[N-(2-hexyldecyloxycarbonyl) amino]-1-ethanol

1st Stage:

105.3 g of carbonyldiimidazole (0.65 mol) were dissolved in 1200 ml of dichloromethane in a two liter reactor.

133.38 g (0.55 mol) of 2-hexyldecanol were then added dropwise over 1 hour at 20° C. The reaction mixture was left stirring for 4 hours at 20° C. The reaction mixture was poured into a separating funnel and washed 4 times with 200 ml of water. The organic phase was dried over sodium sulphate and then concentrated to dryness.

173 g of 2-hexyldecyloxycarbonylimidazole were obtained in the form of a yellow oil.

2nd Stage:

12.2 g (0.2 mol) of aminoethanol were dissolved in 400 ml of anhydrous tetrahydrofuran in a 1 liter reactor. A solution of 73.9 g (0.22 mol) of 2-hexyldecyloxy carbonylimidazole (prepared in the 1st stage) in 300 ml of tetrahydrofuran were added at a temperature of 20° C. over 90 minutes.

Stirring was continued for 24 hours at 20° C. and evaporation was then carried out to dryness. 88 g of an oil were obtained, which oil was dissolved in 500 ml of ethyl acetate and then washed with three times 100 ml of water. The organic phases were combined, dried over sodium sulphate and evaporated to dryness.

71 g of an amber oil were obtained, which oil was purified on silica (9/1 then 8/2 vol/vol heptane/ethyl acetate eluent) to result in 35 g of a colourless oil whose purity was monitored by thin layer chromatography (5/5 vol/vol ethyl acetate/heptane eluent; $R_f=0.55$).

| ELEMENTAL ANALYSIS: | | | | |
|---|---|---|---|---|
| | % C | % H | % O | % N |
| Calculated | 69.30 | 11.85 | 4.25 | 14.58 |
| Found | 69.25 | 11.93 | 4.25 | 14.57 |

EXAMPLE 11

Preparation of 2-[(N-(2-decyltetradecyloxycarbonyl) amino]-1-ethanol

1st Stage:

The preparation was carried out under the same conditions as in the first stage of Example 10, by using:

177 g (0.5 mol) of 2-decyltetradecanol;

89.1 g (0.55 mol) of carbonyldiimidazole; and
1200 ml of dichloromethane.

230 g of 2-decyltetradecyloxycarbonylimidazole were obtained in the form of an amber oil.

2nd Stage:

The preparation was carried out under the same conditions as in the second stage of Example 10, by using:

89.2 g (0.2 mol) of 2-decyltetradecyloxycarbonylimidazole;

13.42 g (0.22 mol) of aminoethanol; and 500 ml of tetrahydrofuran.

73 g of a white wax were obtained, the melting point of which was 48° C.

| ELEMENTAL ANALYSIS: | | | | |
|---|---|---|---|---|
| | % C | % H | % O | % N |
| Calculated | 73.46 | 12.47 | 3.17 | 10.88 |
| Found | 72.94 | 12.49 | 3.32 | 10.92 |

EXAMPLE 12

Shampoo

| | |
|---|---|
| Alkyl ($C_9/C_{10}/C_{11}$-20/40/40) poly(1–4)glucoside sold under the name "APG 300" by the Company Henkel containing 50 g % of active material | 15 g AM |
| Compound of Example 2 | 0.1 g |
| Preserving agents q.s. | |
| Water q.s. for | 100 g |

The pH was adjusted to 7 with hydrochloric acid. A clear fluid solution was obtained.

EXAMPLE 13

Shampoo

| | |
|---|---|
| Sodium lauryl ether carboxylate ($C_{12}/C_{14}$ 70/30) oxyethylenated with 4.5 mol of ethylene oxide as a 22% by weight aqueous solution sold under the name "Akyposoft 45 NV" by the Company Chemy | 7.7 g AM |
| Sodium lauryl ether sulphate ($C_{12}/C_{14}$ 70/30) oxyethylenated with 2.2 mol of ethylene oxide as an 82% by weight aqueous solution sold under the name "Empicol ESB/3FL" by the company Albright & Wilson Saint-Mihiel | 8.5 g AM |
| Coconut acid monoisopropanolamide | 3 g |
| Ether of myristyl glycol and tallow oxyethylenated with 60 mol of ethylene oxide sold under the name "Elfacos GT 2825" by the company Akzo | 0.5 g |
| Compound of Example 8 | 0.8 g |
| Preserving agent q.s. | |
| Water q.s. for | 100 g |

The pH was adjusted to 7 with sodium hydroxide. A clear thickened liquid was obtained.

EXAMPLE 14

Shampoo

| | |
|---|---|
| Sodium lauryl ether carboxylate ($C_{12}/C_{14}$ 70/30) oxyethylenated with 4.5 mol of ethylene oxide as a 22% by weight aqueous solution sold under the name "Akyposoft 45 NV" by the Company Chemy | 15 g AM |
| Sodium lauryl ether sulphate ($C_{12}/C_{14}$ 70/30) oxyethylenated with 2.2 mol of ethylene oxide as an 82% by weight aqueous solution sold under the name "Empicol ESB/3FL" by the Company Albright & Wilson Saint-Mihiel | 8 g AM |
| Coconut acid monoisopropanolamide | 2 g |
| Ether of myristyl glycol and tallow oxyethylenated with 60 mol of ethylene oxide sold under the name "Elfacos GT 2825" by the Company Akzo | 1 g |
| Compound of Example 11 | 0.4 g |
| Preserving agent | 100 g |

The pH was adjusted to 7 with sodium hydroxide. A transparent fluid gel was obtained.

EXAMPLE 15

Shampoo

| | |
|---|---|
| Sodium lauryl ether carboxylate | 15 g AM |
| Mixture of cocoylaminopropyl betaine and of glyceryl monolaurate (25/5) as a 30% by weight aqueous solution sold under the name "Tegobetaine HS" by the Company Goldschmidt | 4 g AM |
| Water/propylene glycol and polyethylene glycol (containing 55 mol of ethylene oxide) dioleate (20/40/40) sold under the name "Antil 141 liquid" by the Company Goldschmidt | 1.2 g AM |
| Compound of Example 3 | 0.3 g |
| Preserving agent q.s. | |
| Water q.s. for | 100 g |

The pH was adjusted to 6.8 with sodium hydroxide. A clear thickened liquid was obtained.

Hair can be shampooed with the compositions of Examples 12 to 15. After drying, it is believed that the hair will be smooth, shiny and easy to disentangle.

EXAMPLE 16

Conditioner

| | |
|---|---|
| Behenyltrimethylammonium chloride at 80% by weight in a water/isopropanol (15/85) mixture sold under the name "Catinal DC 80" by the Company Toho | 2 g AM |
| Compound according to Example 4 | 0.5 g |
| Preserving agents q.s. | |
| Water q.s. for | 100 g |

An opaque fluid solution was obtained.

EXAMPLE 17

Conditioner

| | |
|---|---|
| Cetyltrimethylammonium chloride as a 25% by weight aqueous solution sold under the name "Dehyquart A" by the Company Henkel | 0.5 g AM |
| Compound of Example 5 | 0.5 g |
| Preserving agents q.s. | |
| Water q.s. for | 100 g |

The pH was adjusted to 5.5 with sodium hydroxide.

EXAMPLE 18

Conditioner

| | |
|---|---|
| Behenyltrimethylammonium chloride at 80% by weight in a water/isopropanol (15/85) mixture sold under the name "Catinal DC 80" by the Company Toho | 5 g AM |
| Compound of Example 7 | 0.25 g |
| Preserving agents q.s. | |
| Water q.s. for | 100 g |

A fluid milky solution was obtained.

The conditioners of Examples 16 to 18 can be applied to wet hair after a simple shampooing. After rinsing with water and then drying, it is believed that the hair will be smooth, lively and covered. It is also believed that the styling will have excellent form retention.

EXAMPLE 19

Non-rinsed Lotion

| | |
|---|---|
| Sorbitan monolaurate oxyethylenated with 20 mol of ethylene oxide | 0.5 g |
| Compound of Example 6 | 0.001 g |
| Preserving agents q.s. | |
| Water q.s. for | 100 g |

The pH was adjusted to 7 with sodium hydroxide. A clear fluid lotion was obtained.

EXAMPLE 20

Non-rinsed Lotion

| | |
|---|---|
| 1-Methyl-2-tallow-3-(tallowamidoethyl) imidazolinium methylsulphate as a 75% by weight solution in propylene glycol sold under the name "Rewoquat W 75 PG" by the Company Rewo | 0.2 g AM |
| Compound according to Example 9 | 0.005 g |
| Preserving agent q.s. | |
| Water q.s. for | 100 g |

The pH was adjusted to 5 with sodium hydroxide. An opalescent fluid lotion was obtained.

The lotions of Examples 19 and 20 can be applied to wet hair after a simple shampooing. Without rinsing the hair, it can be dried and then styled. It is believed that the hair will be uniformly smooth, lively, covered and easy to disentangle.

What is claimed is:

1. A cosmetic composition, which comprises at least one compound of formula (I)

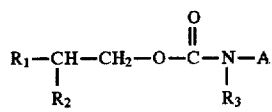

in which:

$R_1$ represents an alkyl or alkylene radical having from 4 to 18 carbon atoms;

$R_2$ represents an alkyl or alkylene radical having from 2 to 16 carbon atoms;

$R_3$ represents a hydrogen atom or an alkyl radical having from 1 to 6 carbon atoms;

A represents a radical of the formula:

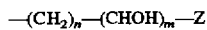

in which:

n represents an integer equal to 0 or 1; m represents an integer ranging from 0 to 5; and wherein Z represents:

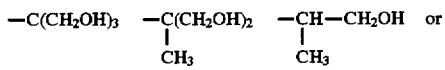

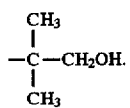

2. A composition according to claim 1, which is provided in the form of an aqueous or aqueous/alcoholic lotion, a gel, a cream, an emulsion, a vesicular dispersion, a foam or a spray.

3. A cosmetic composition according to claim 1, wherein the compound of formula (I) is present at a concentration ranging from 0.001 to 15% by weight with respect to the total weight of the composition.

4. A cosmetic composition according to claim 1, wherein the compound of formula (I) is present at a concentration ranging from 0.1 to 10% by weight with respect to the total weight of the composition.

5. A composition according to claim 1, which is a hair composition.

6. A composition according to claim 5, which is in the form of a shampoo; a conditioner which is or is not to be rinsed; a permanent waving, hair straightening, dyeing or bleaching composition; a composition to be applied before or after dyeing, permanent waving or hair straightening; or a composition for use between the two stages of a permanent wave or a hair straightening.

7. A cosmetic composition according to claim 1, which further comprises at least one cosmetic additive.

8. A method of using the composition according to claim 1, in hair treatment.

9. A method for the treatment of hair comprising the step of applying to hair a composition comprising at least one compound corresponding to formula I:

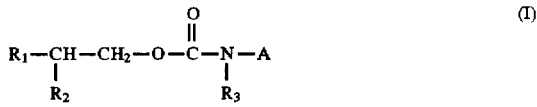

in which:

$R_1$ represents an alkyl or alkylene radical having from 4 to 18 carbon atoms;

$R_2$ represents an alkyl or alkylene radical having from 2 to 16 carbon atoms;

$R_3$ represents a hydrogen atom or an alkyl radical having from 1 to 6 carbon atoms; and A represents a radical of the formula:

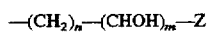

in which:

n represents an integer equal to 0 or 1; m represents an integer ranging from 0 to 5; and wherein Z represents:

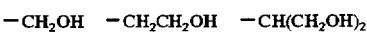

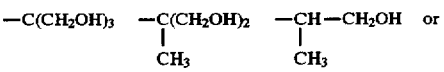

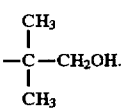

10. A cosmetic composition according to claim 1, wherein $R_1$ represents an alkyl radical having from 4 to 14 carbon atoms; $R_2$ represents an alkyl radical having from 2 to 12 carbon atoms; and $R_3$ represents a hydrogen atom or a methyl radical.

11. A cosmetic composition according to claim 10, wherein the compound is:

N-2-ethylhexyloxycarbonyl-N-methyl-D-glucamine;

N-2-hexyldecyloxycarbonyl-N-methyl-D-glucamine;

N-2-butyloctyloxycarbonyl-N-methyl-D-glucamine;

N-2-decyltetradecyloxycarbonyl-N-methyl-D-glucamine;

N-2-dodecylhexadecyloxycarbonyl-N-methyl-D-glucamine;

N-2-decyltetradecyloxycarbonyl-D-glucamine;

N-2-hexyldecyloxycarbonyl-D-glucamine;

3-[N-(2-decyltetradecyloxycarbonyl)amino]-1,2-propanediol;

2-[N-(2-decyltetradecyloxycarbonyl)amino]-2-hydroxymethyl-1,3-propanediol;

2-[N-(2-hexyldecyloxycarbonyl)amino]-1-ethanol; or

2-[N-(2-decyltetradecyloxycarbonyl)amino]-1-ethanol.

* * * * *